under a first positive pressure of a first fluid in the first pre-valve ullage and the second pre-valve ullage is connected to the post-valve ullage by the second valve under a second positive pressure of a second fluid in the second pre-valve ullage such that the first fluid and the second fluid stored in the first pre-valve ullage and the second pre-valve ullage can be pressed into the post-valve ullage by a first piston and a second piston in order to be injected through the needle being in fluid communication with the second end of the post-valve ullage.

20 Claims, 10 Drawing Sheets

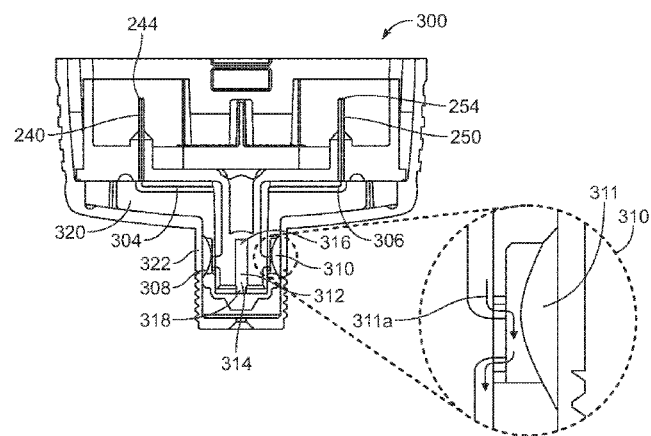

and the second pre-valve ullage is connected to the post-valve ullage by the second valve. A first fluid is guidable from the first pre-valve ullage to the post-valve ullage and a second fluid is guidable from the second pre-valve ullage to the post-valve ullage.

10 Claims, 10 Drawing Sheets

(51) Int. Cl.
*A61M 5/24* (2006.01)
*A61M 5/31* (2006.01)

(58) Field of Classification Search
CPC ............... A61M 5/3129; A61M 5/315; A61M 5/31525; A61M 5/322; A61M 5/34
See application file for complete search history.

(56) References Cited

U.S. PATENT DOCUMENTS

| | | | | |
|---|---|---|---|---|
| 4,673,395 | A | * | 6/1987 | Phillips .................. 604/191 |
| 4,689,042 | A | * | 8/1987 | Sarnoff ............... A61M 5/2066 604/136 |
| 4,874,368 | A | * | 10/1989 | Miller et al. .................. 604/82 |
| 4,978,336 | A | * | 12/1990 | Capozzi et al. ............... 604/82 |
| 5,104,375 | A | * | 4/1992 | Wolf et al. ................. 604/518 |
| 5,147,323 | A | * | 9/1992 | Haber et al. ................. 604/191 |
| 5,226,895 | A | | 7/1993 | Harris |
| 5,240,146 | A | * | 8/1993 | Smedley ................ A61M 5/19 222/137 |
| 5,271,527 | A | * | 12/1993 | Haber et al. ..................... 222/43 |
| 5,279,586 | A | | 1/1994 | Balkwill |
| 5,298,023 | A | * | 3/1994 | Haber ................ A61M 5/2448 604/191 |
| 5,304,152 | A | | 4/1994 | Sams |
| 5,314,412 | A | * | 5/1994 | Rex ................. 604/191 |
| 5,320,609 | A | | 6/1994 | Haber et al. |
| 5,383,865 | A | | 1/1995 | Michel |
| 5,478,323 | A | * | 12/1995 | Westwood ............. A61M 5/19 604/191 |
| 5,480,387 | A | | 1/1996 | Gabriel et al. |
| 5,505,704 | A | * | 4/1996 | Pawelka et al. ............. 604/191 |
| 5,582,598 | A | | 12/1996 | Chanoch |
| 5,626,566 | A | | 5/1997 | Petersen et al. |
| 5,674,204 | A | | 10/1997 | Chanoch |
| 5,688,251 | A | | 11/1997 | Chanoch |
| 5,814,022 | A | * | 9/1998 | Antanavich et al. ......... 604/191 |
| 5,921,966 | A | | 7/1999 | Bendek et al. |
| 5,961,495 | A | | 10/1999 | Walters et al. |
| 6,004,297 | A | | 12/1999 | Steenfeldt-Jensen et al. |
| 6,193,698 | B1 | | 2/2001 | Kirchhofer et al. |
| 6,221,046 | B1 | | 4/2001 | Burroughs et al. |
| 6,235,004 | B1 | | 5/2001 | Steenfeldt-Jensen et al. |
| 6,248,095 | B1 | | 6/2001 | Giambattista et al. |
| 6,471,670 | B1 | * | 10/2002 | Enrenfels et al. ............. 604/88 |
| 6,899,698 | B2 | | 5/2005 | Sams |
| 6,936,032 | B1 | | 8/2005 | Bush, Jr. et al. |
| 7,241,278 | B2 | | 7/2007 | Moller |
| 7,955,301 | B1 | * | 6/2011 | McKay ..................... 604/121 |
| 2002/0052578 | A1 | | 5/2002 | Moller |
| 2002/0120235 | A1 | | 8/2002 | Enggaard |
| 2003/0050609 | A1 | | 3/2003 | Sams |
| 2004/0059299 | A1 | | 3/2004 | Moller |
| 2004/0210199 | A1 | | 10/2004 | Atterbury et al. |
| 2004/0267207 | A1 | | 12/2004 | Veasey et al. |
| 2005/0113765 | A1 | | 5/2005 | Veasey et al. |
| 2006/0153693 | A1 | | 7/2006 | Fiechter et al. |
| 2007/0073267 | A1 | * | 3/2007 | Muller ..................... 604/506 |
| 2007/0088271 | A1 | * | 4/2007 | Richards ................... 604/151 |
| 2008/0185056 | A1 | | 8/2008 | Diodati et al. |
| 2008/0262469 | A1 | * | 10/2008 | Brister et al. ............... 604/504 |
| 2009/0275916 | A1 | | 11/2009 | Harms et al. |
| 2011/0184350 | A1 | * | 7/2011 | McKay ..................... 604/174 |

FOREIGN PATENT DOCUMENTS

| | | |
|---|---|---|
| EP | 2335755 | 6/2011 |
| JP | H06-505411 | 6/1994 |
| JP | H08-503385 | 4/1996 |
| JP | H08-503874 | 4/1996 |
| JP | H10-511014 | 10/1998 |
| WO | 92/10425 | 6/1992 |
| WO | 92/15345 | 9/1992 |
| WO | WO 92/15345 * | 9/1992 |
| WO | 96/14097 | 5/1996 |
| WO | 99/38554 | 8/1999 |
| WO | 01/10484 | 2/2001 |

OTHER PUBLICATIONS

Translation of Chinese Office Action for CN App. No. 201280031661.X, dated Feb. 15, 2016.
Translation of Chinese Office Action for CN App. No. 201280031661.X, dated May 6, 2015.

* cited by examiner

VALVE ARRANGEMENT FOR MEDICAL DEVICE

CROSS REFERENCE TO RELATED APPLICATIONS

The present application is a U.S. National Phase application pursuant to 35 U.S.C. §371 of International Application No. PCT/EP2012/057682 filed Apr. 26, 2012, which claims priority to U.S. Provisional Patent Application No. 61/480,063 filed Apr. 28, 2011, and European Patent Application No. 11173269.9 filed Jul. 8, 2011. The entire disclosure contents of these applications are herewith incorporated by reference into the present application.

FIELD OF DISCLOSURE

The present patent application relates to medical devices for delivering at least two drug agents from separate reservoirs. Such drug agents may comprise a first and a second medicament. The medical device includes a dose setting mechanism for delivering the drug agents automatically or manually by the user.

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

BACKGROUND

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then only combined and/or delivered to the patient during a single delivery procedure. These active agents may be administered together in a combined dose or alternatively, these active agents may be combined in a sequential manner, one after the other.

SUMMARY

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g., a double ended needle assembly) into the desired injection site. The dose of the combination of the primary compound and the secondary compound (and potentially a third medicament) is administered by activating an injection user interface (e.g., an injection button).

Both medicaments may be delivered via one injection needle or dose dispenser and in one injection step. This offers a convenient benefit to the user in terms of reduced user steps compared to administering two separate injections.

Using a single device and especially using a single injection needle to reduce the normally two injection steps to a single step generates the problem of an uncontrolled mixture of the two drug agents used.

It is always necessary for a successful therapy to deliver the two different drug agents to the patient in a very particular dose. Since the two drug agents share a common injection needle the two different drug agents need to mix at some point in the medical device, in case the two drug agents are administered in a combined dose. Due to the comparable big volumes and long paths the drug agents need to pass between the reservoirs and the injection site an uncontrollable mixture of the medicaments can often not be avoided, producing an uncertainty on the exact dose administered.

In case the two drug agents are administered in a sequential manner one after another, there is also an uncertainty over the exact dose administered, especially the exact dose of the second drug agent, since the fluidic channels in the drug delivery device are of course at least partially filled with remainders of the first drug agents, leading again to an uncontrolled mixing of the two medicaments.

The invention faces the technical problem of reducing the uncertainty over exact doses ejected from a medical device and reducing the risk of cross-contamination of the two or more medicaments.

The technical problem is solved by a medical device comprising a first valve, a second valve, a first pre-valve ullage, a second pre-valve ullage, a post-valve ullage with a first end and a second end and a needle. The first pre-valve ullage is connected to the post-valve ullage by the first valve and the second pre-valve ullage is connected to the post-valve ullage by the second valve. A first fluid is guidable from the first pre-valve ullage to the post-valve ullage and a second fluid is guidable from the second pre-valve ullage to the post-valve ullage. A first end of the needle is inserted into the post-valve ullage and the post-valve ullage is designed such that there is a flow inversion between the post-valve ullage and the needle.

By providing two separate valves for each of the at least two fluids, the fluids are kept separate in their own pre-valve ullages. This limits the region, where the different fluids can mix, to the post-valve ullage. It has been found that this way a much more precise, controlled and predictable mixture of the different fluid, in particular drug agents, can be ejected from the medical device. Of course, the pre-valve ullages do not have a direct connection to each other apart from their connection to the common post-valve ullage over the respective valves.

The two separate valves for each fluid also prevent the first fluid to be pushed into the second pre-valve ullage or even further back, for example into a reservoir for the second fluid and vice versa.

In case the fluids are ejected from the medical device one after another, the inventive medical device improves the uncertainty over exact doses, since the common fluidic passage is reduced to the post-valve ullage. That means that the amount of the first fluid remaining in the common fluidic passage is effectively reduced, thus providing a better control of the second dose.

The volume of the post-valve ullage though is still sufficient to provide a region, in which both medicaments can mix sufficiently, so that a homogeneous mixture of the fluids is provided in case the fluids are ejected together.

According to another embodiment the medical device further comprises a first reservoir and a second reservoir, wherein the first reservoir is connected to the first pre-valve ullage and the second reservoir is connected to the second pre-valve ullage. These reservoirs provide separate storage vessels for the first and second fluid. This is particularly useful for drug agents, which must not be stored together or in a ready-made mixture. This way, the fluids, in particular drug agents, mix in the post-valve ullage for the first time, right before the mixture is ejected from the medical device and/or injected at the injection site, for example.

The reservoirs are preferably detachably attached to the respective pre-valve ullages. This connection can in particular be provided by needles or cannulas, which are preferably made from metal, for example steel. This accounts for the fact, that the reservoirs might be exchanged with different frequencies than the part of the medical device containing said ullages and valves.

The first and second pre-valve ullages can be in constant fluid communication with the respective reservoir. The valves prevent the fluids to enter the post-valve ullage while the medical device is not used.

According to another embodiment of the medical device, a first end of the needle is inserted into the post-valve ullage at the second end of the post-valve ullage. This provides a simple possibility to guide either fluid or a mixture of both fluids to an injection site. No further guiding by complicated fluidic systems is needed and the overall fluidic system from the reservoir to the injection site, in particular from the post-valve ullage to the injection site is minimized. This further reduces unnecessary volume for the fluids to pass and improves the accuracy of the doses. The needle is preferably made of metal, in particular steel, to provide a biocompatible material and to be able to directly inject the fluids into the skin of a user, for example.

Such a needle can in particular be a double ended needle, which can be attached to the medical device, providing an exchangeable injection needle.

It is further preferred when the first end of the needle is substantially in the center of the post-valve ullage. On the one hand, this reduces the danger of damaging the post valve ullage with the first end of the needle.

On the other hand, this provides a flow inversion and thus further improves the flow efficiency. The fluids enter the post-valve ullage, for example at its first end or at its second end, and the fluids exit the post-valve ullage through the needle in or near the center or at or near an opposite end of the post-valve ullage. This configuration makes the fluid change directions and thus provides an excellent mixing of the fluids and an improved flow-out. This effect is especially distinct, when the fluids enter the post-valve ullage at its second end, since the flow directions of the fluids during entering and exiting the post-valve ullage are anti-parallel.

According to another embodiment of the medical device, the first fluid and/or the second fluid enter the post-valve ullage substantially tangentially. That means, if the post valve ullage has a substantially cylindrical shape for example, the first fluid and/or the second fluid enter the post-valve ullage tangentially to its curved surface area. In this way, a particularly effective mixing of the fluids can be achieved.

According to the invention the post-valve ullage is designed such that there is a flow inversion between the post valve ullage and the needle. This effect can in particular be achieved by providing a post-valve ullage, into which the fluids enter at the second end of the post-valve ullage, while the first end of the needle is located in or near the center or at or near the first end of the post-valve ullage. This results in the effect that the fluids flow into the post-valve ullage substantially from the second end towards the first end of the post-valve ullage and exit the post-valve ullage through the first end of the needle flowing substantially from the first end of the post valve ullage in the direction of the second end of the post valve ullage. Thus, an antiparallel upward and downward movement of the fluids provides in this case the flow inversion and therefore an effective mixing of the fluids.

The same effect is achieved in case the fluids enter the post valve ullage at the first end of the post-valve ullage for example, since at least a part of the fluids will reach the second end of the post-valve ullage and the fluids will have to flow towards the first end of the post-valve ullage to reach the center of the post-valve ullage and to exit through the first end of the needle. Thus, a flow inversion is achieved in the post-valve ullage and a particularly effective mixing of the fluids can be achieved.

According to another embodiment of the medical device, it is advantageous, when the first pre-valve ullage and the second pre-valve ullage are provided by an inner body and the first valve and the second valve are provided by a first and a second elastic part respectively adjacent to an outer body of the medical device.

This facilitates the production of the medical device. The valve is provided between outer and inner body, such that no stand-alone parts are necessary in this arrangement as for example for diaphragm valves. The first and second elastic parts seal the fluidic connection between the respective pre-valve ullages and the post-valve ullage.

Preferably, the elastic parts have flexible portions such that the flexible portions can move freely and the valves are opened and closed depending on the pressure of the respective fluids in the pre-valve ullages. If the pressure is high enough in the first pre-valve ullage, the flexible portion is preferably pushed out of the way opening the first valve and establishing a fluid connection between the first pre-valve ullage and the post valve ullage. The second valve can work in the same way. Though, it is also possible that the valves are activated automatically by a mechanical mechanism, for example.

Preferably the valves are of such design, that the valve is a one way valve and a backpressure from the post-valve ullage cannot open the valves.

Such a so called "sleeve valve" can be easily implemented by a circular diaphragm valve, for example.

The elastic part might also be designed integrally with the outer body of the medical device.

It is preferred, when the post-valve ullage is configured such that the fluid enters the post-valve ullage at the second end of the post valve ullage. The fluid can be guided to the second end of the post-valve ullage by fluidic channels connecting the respective valve with the second end of the post-valve ullage. This way a more homogenous mixing of the fluids can be achieved and an efficient guiding of the fluids with a minimal length of the fluidic system, since the fluids do not need to be guided to the first end of the post-valve ullage again. This further promotes the reduction of the uncertainty over exact doses ejected, while at the same time a homogeneous, but controlled mixture is provided.

According to another embodiment of the Medical device, the first valve and the second valve are provided by valves located at the first end of the post-valve ullage. This arrangement provides a minimal channel length from the pre-valve ullages or the reservoirs to the post-valve ullage or the injection site. This further reduces the uncertainty over exact doses ejected from the medical device and at the same time provides a homogeneous, but controlled mixture of two fluids.

The valves can be designed as standard umbrella or diaphragm valves, but may preferably be designed as so called "beak valves". Such beak valves are substantially funnel shaped with a point-shaped opening or an opening in form of a slit. In the closed state the elastic material adjacent to the opening is pre-stressed such that the opening is closed. The pressure of the fluid can open force the elastic material aside, so that the beak valve opens.

It is especially preferred, when the first valve is configured to be controlled by the pressure of the fluid in the first pre-valve ullage and/or the second valve is configured to be controlled by the pressure of the fluid in the second pre-valve ullage. This provides a very simple and cost-sensitive implementation of the valves into the medical device, because no external control of the valves is necessary, for example by mechanical actuators or the like.

It is especially preferred when the first valve and/or the second valve is at least in part made from one or more materials selected from the group of TPE, PTFE, silicone and EPDM. These materials are especially suitable since they show a high biocompatibility, for example requirements for sterilization, and at the same time provide a sufficient sealing function between the pre-valve ullage and the post-valve ullage.

Valves from thermoplastic elastomers (TPE) are especially easy to produce since they can be molded and only little or no compounding is necessary to achieve the desired material properties.

Polytetrafluoroethylene (PTFE) shows a very low coefficient of friction optimizing the fluidic properties of the medical device. Moreover PTFE is subjected to material creep, which can be advantageous when used in valves and seals, since the valve or seal creeps a certain amount and can thus match the corresponding counter-surface to establish a tight seal.

Silicone is readily tested in medical appliances and provides good sealing properties combined with good biocompatibility.

Valves made from ethylene propylene diene monomer rubber (EPDM) provide a high resistivity against humidity and ozone. Furthermore EPDM has a high chemical stability and a high elasticity, providing excellent properties for sealing applications.

In particular the medical device is a drug delivery system. Especially for drug delivery systems it is of utmost importance to reduce the uncertainty over exact doses ejected and at the same time providing a homogeneous, but controlled mixture of the ejected fluids.

It is especially advantageous if the medical device further comprises a dispense interface comprising the first valve, the second valve, the first pre-valve ullage, the second pre-valve ullage and the post-valve ullage with the first end and said second end. The dispense interface can hence be exchanged or replaced independently from the rest of the medical device, especially a cartridge holder, containing the first and second reservoir.

BRIEF DESCRIPTION OF THE FIGURES

These as well as other advantages of various aspects of the present invention will become apparent to those of ordinary skill in the art by reading the following detailed description, with appropriate reference to the accompanying drawings, in which.

DETAILED DESCRIPTION

Figure 1:
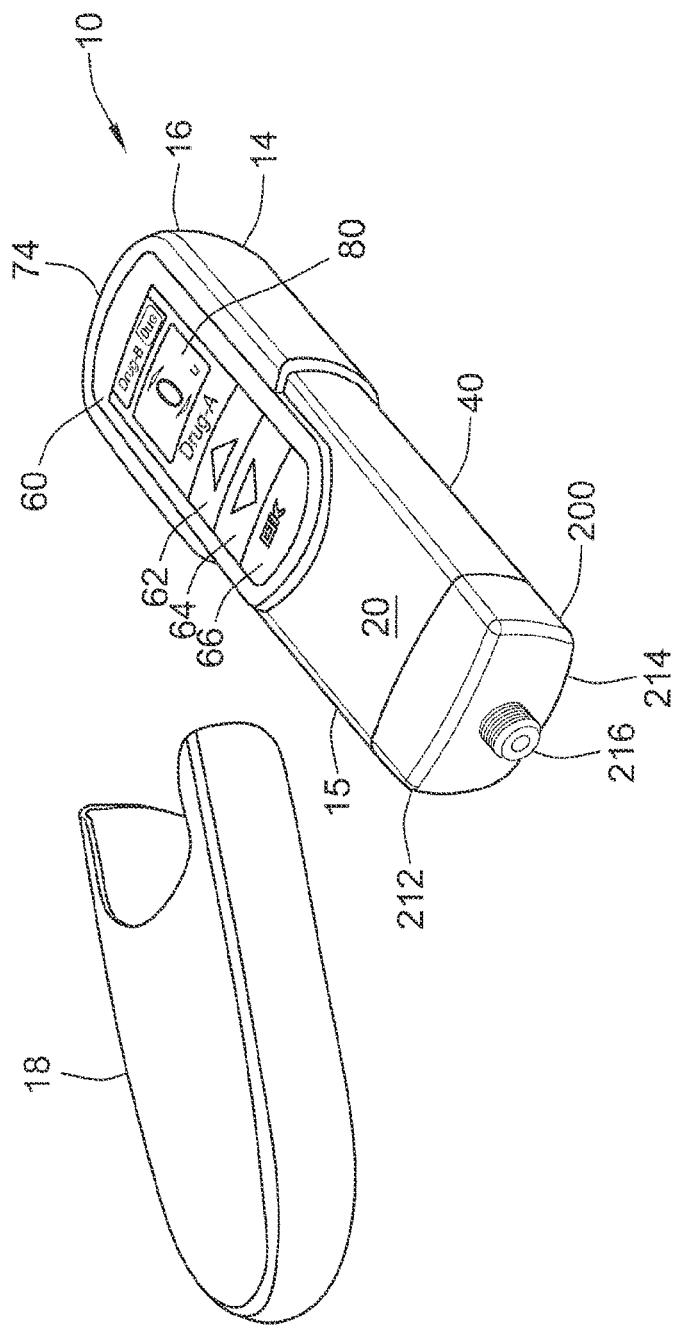
FIG. 1 illustrates a perspective view of a delivery device with an end cap of the device removed.

The drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1).

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 212 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
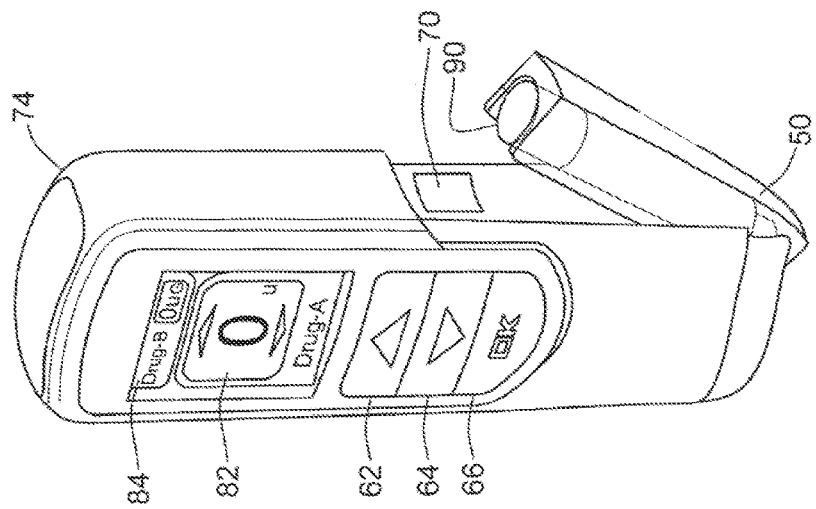
FIG. 3 illustrates a perspective view of the delivery device illustrated in FIG. 1 or 2 with one cartridge retainer in an open position.
Figure 2:
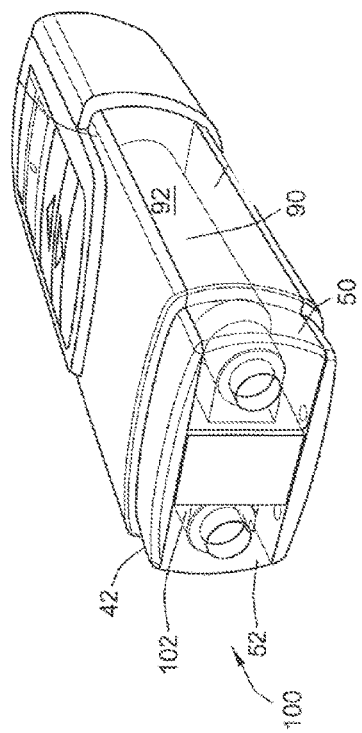
FIG. 2 illustrates a perspective view of the delivery device distal end showing the cartridge.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
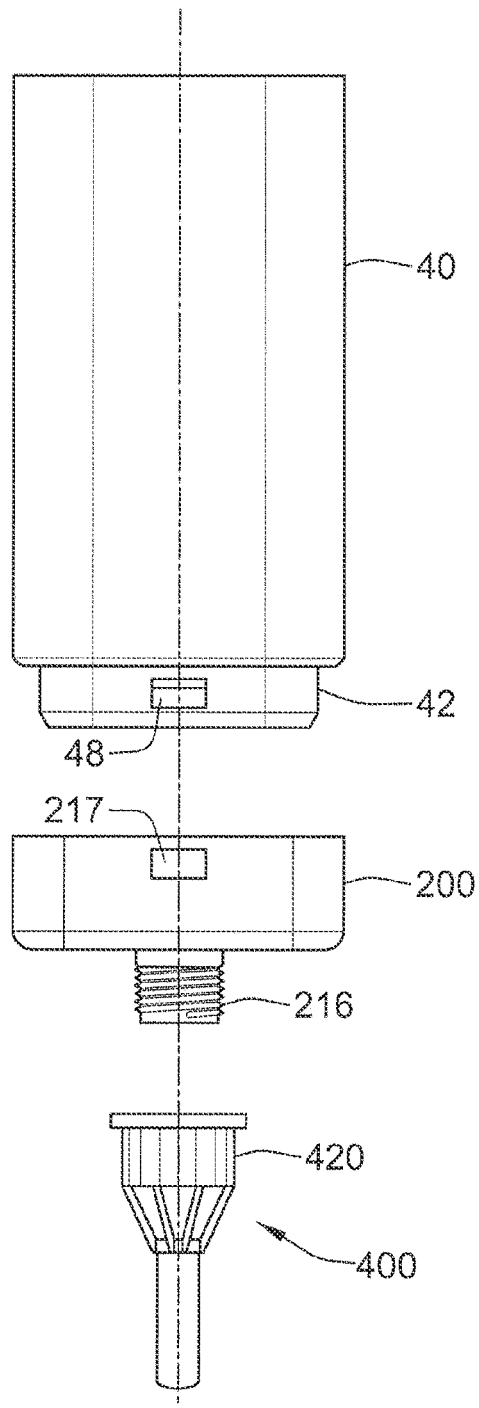
FIG. 4 illustrates a dispense interface and a dose dispenser that may be removably mounted on a distal end of the delivery device illustrated in FIG. 1.

As mentioned above when discussing FIG. 1, a dispense interface 200 is coupled to the distal end of the cartridge holder 40. FIG. 4 illustrates a flat view of the dispense interface 200 unconnected to the distal end of the cartridge holder 40. A dose dispenser or needle assembly 400 that may be used with the interface 200 is also illustrated and is provided in a protective outer cap 420.

Figure 5:
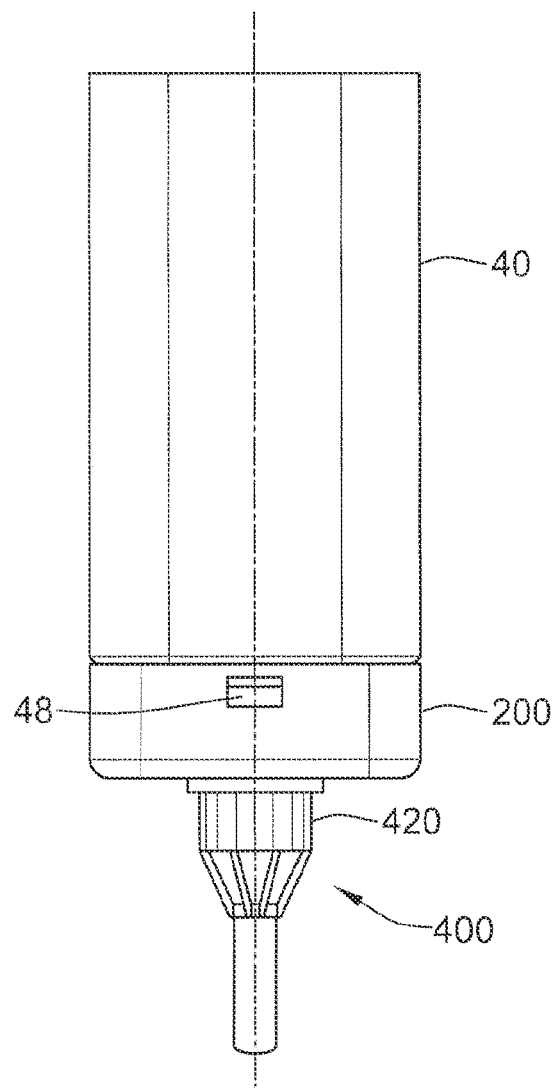
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
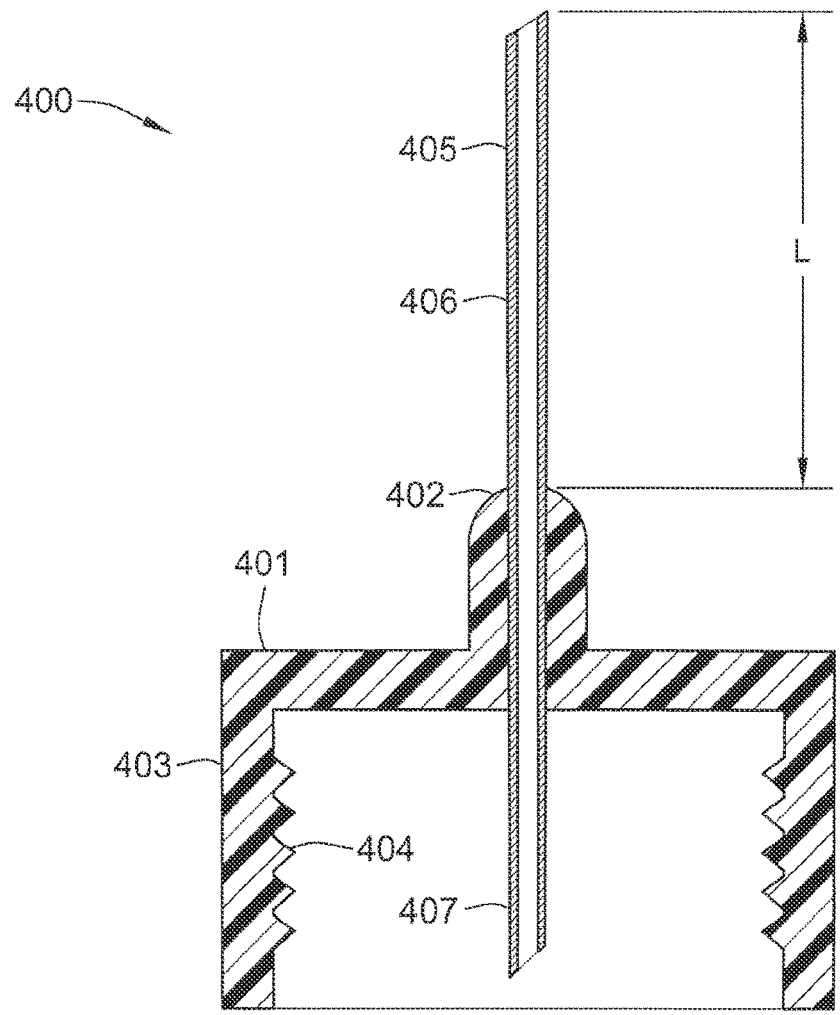
FIG. 6 illustrates a needle assembly that may be mounted on a distal end of the delivery device.
Figure 7:
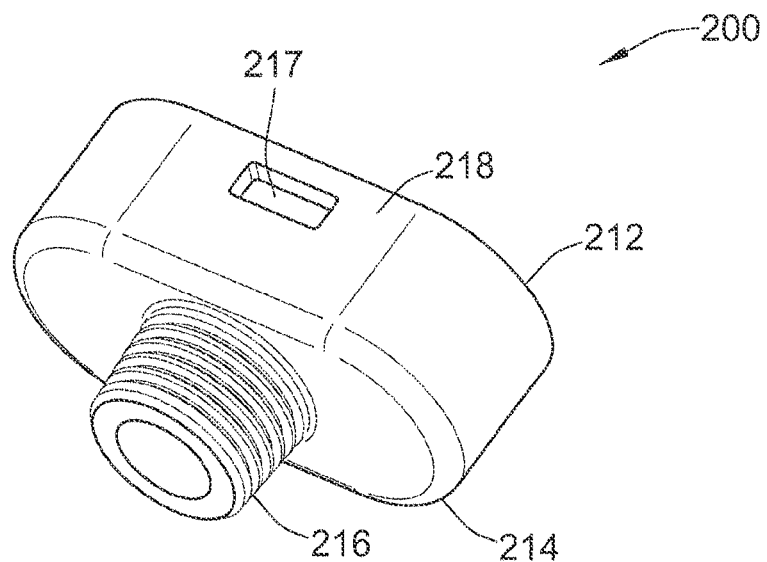
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 402 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 406 of the needle assembly 400 protrudes from an opposite side of the circular disc so that it is concentrically surrounded by the sleeve 403. In one needle assembly arrangement, the second or proximal piercing end 406 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
b. an first inner body 220,
c. a second inner body 230,
d. a first piercing needle 240,
e. a second piercing needle 250,
f. a valve seal 260, and
g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213*a* and a second rib 213*b*. This first rib 213*a* is also illustrated in FIG. 10. These ribs 213*a* and 213*b* are positioned along the inner surface 215 of the wall 218 of the outer body 210 and create a form fit or snap lock engagement with cooperating grooves 224*a* and 224*b* of the first inner body 220. In a preferred arrangement, these cooperating grooves 224*a* and 224*b* are provided along an outer surface 222 of the first inner body 220.

Figure 8:
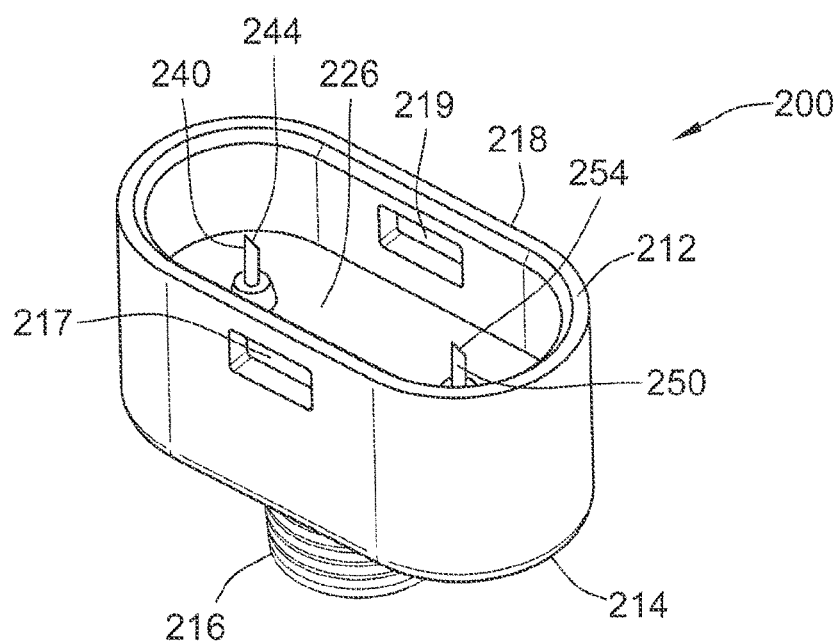
FIG. 8 illustrates another perspective view of the dispense interface illustrated in FIG. 4.
Figure 9:
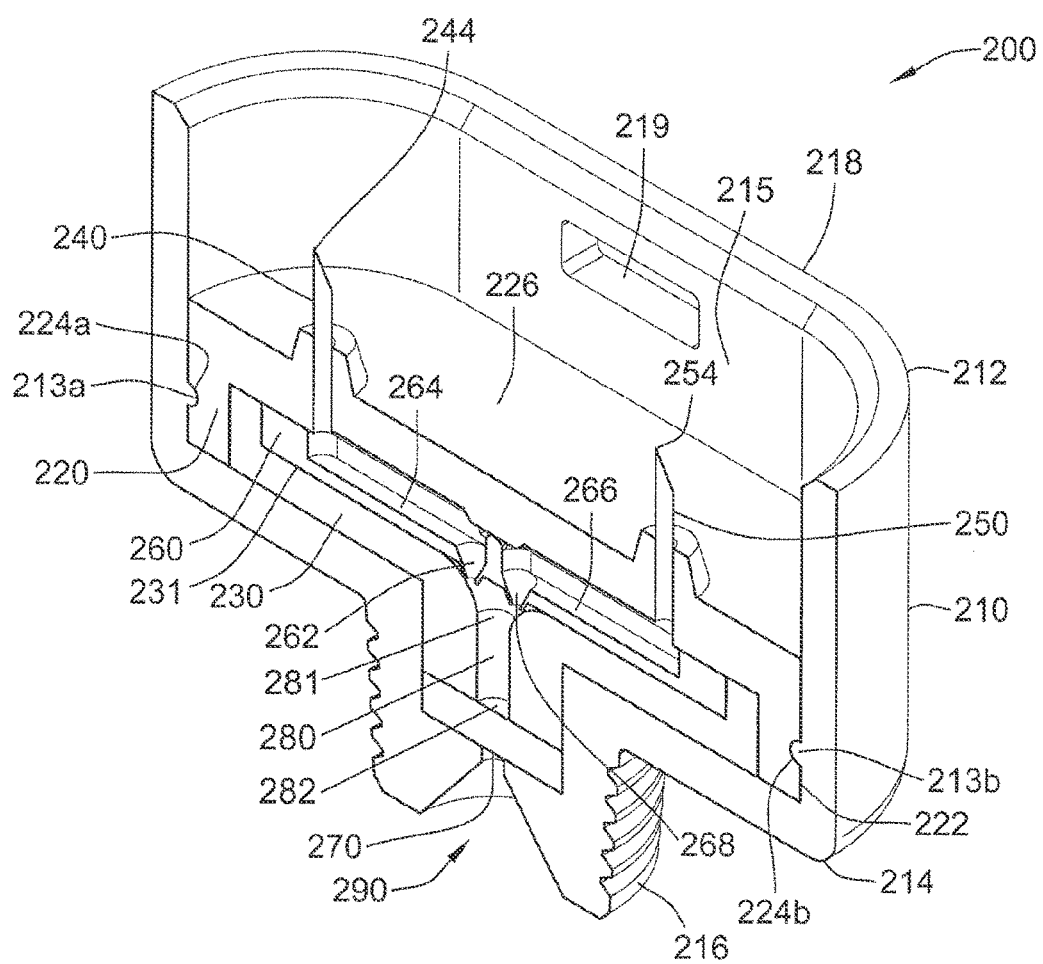
FIG. 9 illustrates an exemplary embodiment of the invention in a cross-sectional view of the dispense interface illustrated in FIG. 4.
Figure 10:
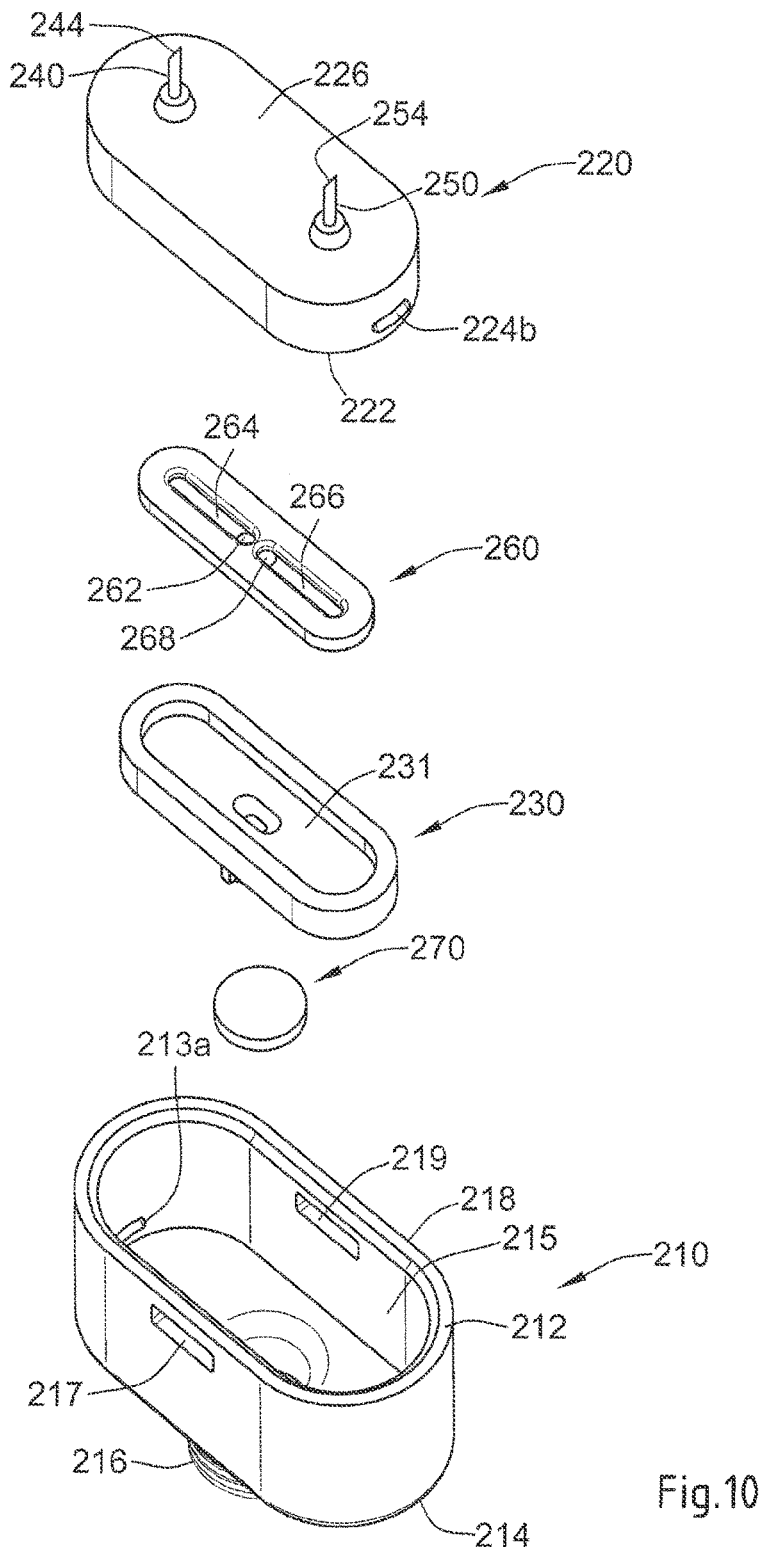
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. The valve arrangement is constructed so as to prevent cross contamination of the first and second medicaments contained in the first and second reservoirs, respectively. Additionally, the valve arrangement is also configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove or a first pre-valve ullage 264 and second fluid groove or a second pre-valve ullage 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. This seal valve 260 comprises a first non-return valve 262 and a second non-return valve 268. As such, the first non-return valve 262 prevents fluid transferring along the first fluid pathway or first pre-valve ullage 264, for example a groove in the seal valve 260, from returning back into this pathway or pre-valve ullage 264. Similarly, the second non-return valve or second pre-valve ullage 268 prevents fluid transferring along the second fluid pathway or second pre-valve ullage 266 from returning back into this pathway or pre-valve ullage 266.

Together, the first and second grooves or pre-valve ullages 264, 266 converge towards the non-return valves 262 and 268 respectively, to then provide for an output fluid path or a post-valve ullage in form of a holding chamber 280. This holding chamber 280 is defined by an inner chamber defined by a distal end of the second inner body, a first end 281 with both the first and the second non return valves 262, 268 and a second end 282 with a pierceable septum 270. As illustrated, this pierceable septum 270 is positioned between a distal end portion of the second inner body 230 and an inner surface defined by the needle hub of the main outer body 210.

The holding chamber or post-valve ullage 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove or first pre-valve ullage 264 and the second groove or second pre-valve ullage 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
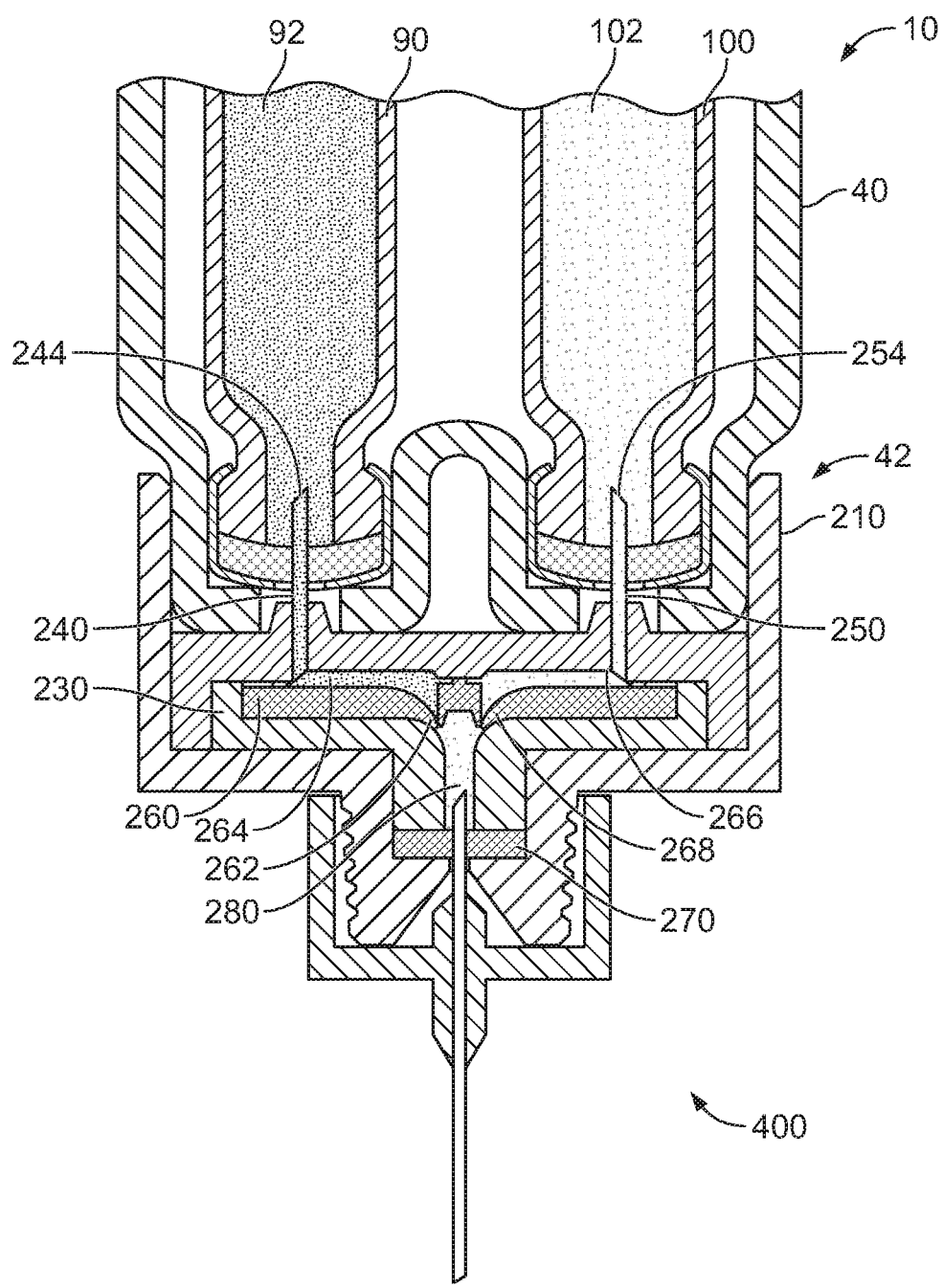
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber or post-valve ullage 280 is illustrated as being in fluid communication with a dose dispenser. Here, as illustrated, this dose dispenser comprises the double ended needle assembly 400. As illustrated, the proximal end of the double ended needle assembly is in fluid communication with the ullage 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
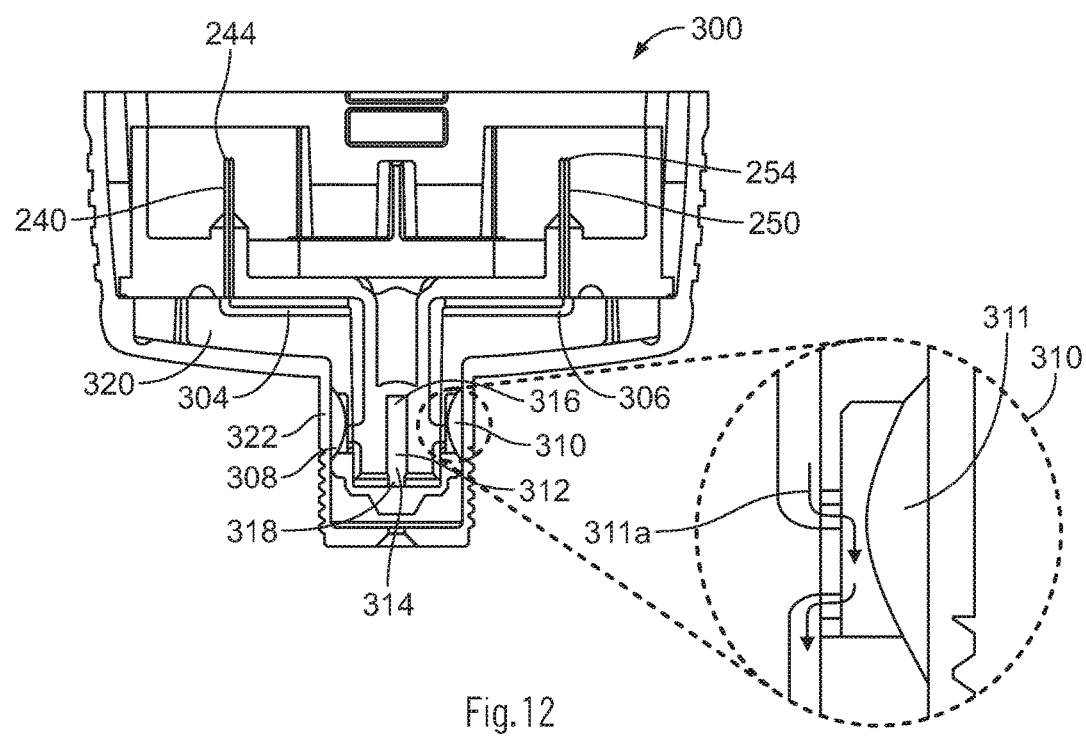
FIG. 12 illustrates another exemplary embodiment according to the invention in a cross sectional view.

In an alternative valve arrangement, the dispense interface may comprise a valve arrangement comprising a sleeve valve arrangement. For example, FIG. 12 illustrates a cross sectional view of an alternative valve arrangement for use in a dispense interface 200. In this arrangement, the dispense interface 300 comprises a sleeve valve arrangement 302.

As illustrated, the dispense interface 300 comprises a first medicament pre-valve ullage 304 and a second medicament pre-valve ullage 306. The first medicament pre-valve ullage 304 would contain ullage of the first medicament residing between the cartridge containing the first medicament and the first medicament valve 308. Similarly, the second medicament pre-valve ullage 306 would contain ullage of the second medicament residing between the cartridge containing the second medicament and the second medicament valve 310.

As in the valves of 308 and 310, the flexible portion 311 of the elastic part is not jacked up by the outer housing of the dispense interface 300. As such, these flexible portions 311 are free to flexibly move and are driven by pressure/backpressure, similar to the valve arrangement illustrated in FIG. 9. The flexible portions 311 are connected to the rest of the elastic component and, in this arrangement, do not comprise stand-alone components other solutions in the state of the art. FIG. 12 shows a blow-up view of the valve 310 where flow direction arrows 311a indicate the flow of fluid through valve 310 due to movement of the flexible portion 311 of the valve 310.

The post valve ullage 312 is provided as a holding chamber 314 of the dispense interface 300. In this arrangement, both the first and the second cartridges contained within the drug delivery device comprise their own one-way valve that connect to a shared post valve ullage. Once a dispenser, such as a double ended needle assembly, is mounted to the distal end of the dispense interface, the shared post valve ullage would be in fluid communication with this dispenser acting as an outlet needle.

The post-valve ullage 312 has a first end 316 and a second end 318. In this embodiment the medicaments enter the post-valve ullage 312 through the second end 318. The end of a double ended needle 406 can be inserted through the same end 318.

Figure 13:
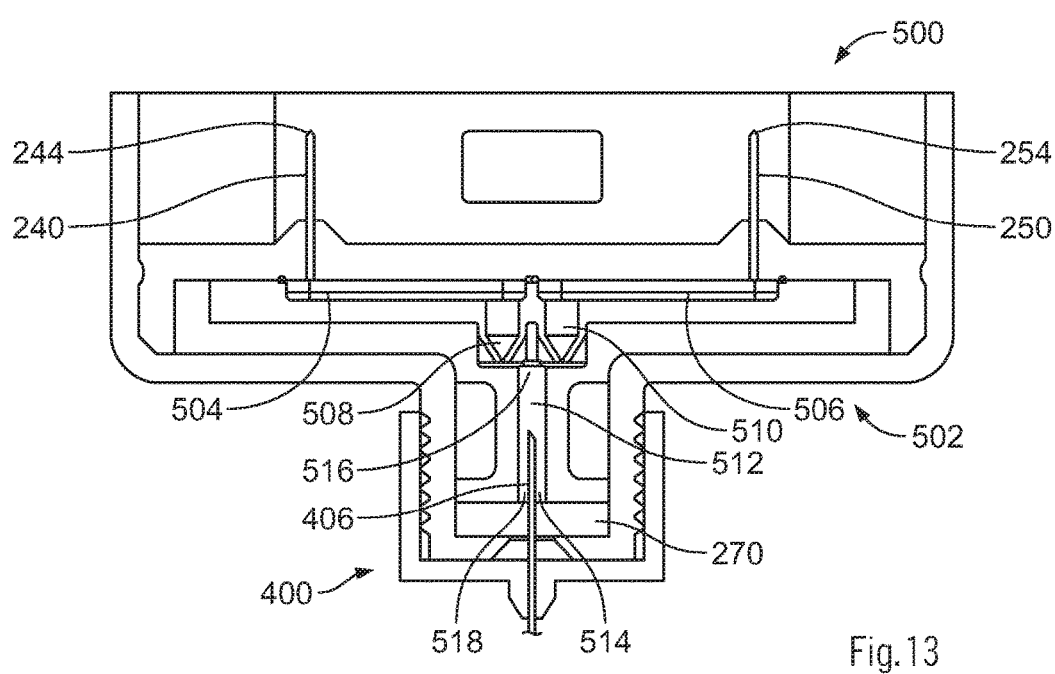
FIG. 13 illustrates another exemplary embodiment according to the invention in a cross sectional view.

As can be further seen from FIG. 12, the ullages are provided by the inner body 320, while the valves are positioned between the inner body 320 and the outer body 322. Here, the drug agents 92, 102 are guided past the post-valve ullage 312 to be inserted into the post-valve ullage 312 at the second end 318 of the post-valve ullage 312. A needle 406 as illustrated in FIG. 13 is usually already inserted in to the post valve ullage 312. This results in the effect that the drug agents 92, 102 flow into the post-valve ullage 312 substantially from the second end 318 towards the first end 316 of the post valve ullage 312 and exit the post-valve ullage 312 through the first end 405 of the needle 406 substantially from the first end 316 of the post valve ullage 312 in the direction of the second end 318 of the post valve ullage 312. Thus, a flow inversion is achieved in the post-valve ullage 312 and a particularly effective mixing of the drug agents 92, 102 can be achieved.

Alternatively, the dispense interface may comprise a valve arrangement comprising a beak valve arrangement. For example, FIG. 13 illustrates a cross sectional view of a beak valve arrangement 502 for use in a dispense interface 500. As illustrated, the dispense interface 500 comprises a first medicament pre-valve ullage 504 and a second medicament pre-valve ullage 506. In this arrangement, both the first and the second cartridges contained within the drug delivery device comprise a separate own one-way valve. For example, the first cartridge containing the primary medicament would comprise the first one-way valve 508 and the second cartridge containing the secondary medicament would contain the second one-way valve 510. In this arrangement, both the first and the second cartridges contained within the drug delivery device comprise their own one-way valve that connect to a shared post valve ullage 512 in form of a holding chamber 514. Once a doser, such as a double ended needle assembly, is mounted to the distal end of the dispense interface, the shared post valve ullage would be in fluid communication with this dispenser acting as an outlet needle.

In this case the drug agents enter the post-valve ullage 512 through the first end 516. As can be further seen from FIG. 13, the first end 407 of the needle 406 is positioned substantially in the middle of the post-valve ullage 512. Thus, while the drug agents 92, 102 enter the post valve ullage 512 at the first end 516 of the post-valve ullage 512 and at least a part of the drug agents 92, 102 will reach the second end 518 of the post-valve ullage 512, the drug agents 92, 102 have to exit through the first end 405 of the needle 406 and therefore will have to flow again towards the first end 516 of the post-valve ullage 512 to reach the center of the post-valve ullage 512. Thus, a flow inversion is achieved in the post-valve ullage 512 and a particularly effective mixing of the drug agents 92, 102 can be achieved.

In particular the valves 308, 310, 508, 510 illustrated in FIGS. 12 and 13, can be made of a material such as TPE, PTFE, silicone or EPDM.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39), des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. Medical device comprising:
a first valve,
a second valve,
a first pre-valve ullage,
a second pre-valve ullage,
a first proximally positioned piercing needle,
a second proximally positioned piercing needle,
a post-valve ullage configured as a holding chamber having a first proximal end and a second distal end, and
a needle having a first proximal end inserted into the second distal end of the holding chamber,
wherein said first pre-valve ullage is connected to said post-valve ullage by said first valve,
wherein said second pre-valve ullage is connected to said post-valve ullage by said second valve,
wherein a first fluid is guidable from a first cartridge containing the first fluid via the first proximally positioned piercing needle to the first pre-valve ullage, from the first pre-valve ullage through the first valve, and then to the second distal end of the post-valve ullage,
wherein a second fluid is guidable from a second cartridge containing the second fluid via the second proximally positioned piercing needle to the second pre-valve ullage, from the second pre-valve ullage through the second valve, and then to the second distal end of the post-valve ullage, and
wherein the holding chamber is configured such that the first and the second fluid enter the holding chamber at the second distal end flowing towards the first proximal end and are mixed in the holding chamber before exiting the first distal end of the post-valve ullage and prior to administering the first and second fluids through the needle, and wherein the first and second fluids enter at different sides of the holding chamber respectively.

2. Medical device according to claim 1, further comprising a first reservoir and a second reservoir, wherein said first reservoir is connected to said first pre-valve ullage and said second reservoir is connected to said second pre-valve ullage.

3. Medical device according to claim 1, wherein said first proximal end of said needle is in the center of said post-valve ullage.

4. Medical device according to claim 1, wherein the first fluid and/or the second fluid enter the post-valve ullage substantially tangentially.

5. Medical device according to claim 1, wherein said first pre-valve ullage and said second pre-valve ullage are provided by an inner body and said first valve and said second valve are provided by a first elastic part and a second elastic part adjacent to an outer body of said medical device.

6. Medical device according to claim 1, wherein said first valve and said second valve are provided by valves located by the first proximal end of the post-valve ullage.

7. Medical device according to claim 1, wherein said first valve is configured to be controlled by a pressure of said first fluid in said first pre-valve ullage and/or said second valve is configured to be controlled by a pressure of said second fluid in said second pre-valve ullage.

8. Medical device according to claim 1, wherein the first valve and/or the second valve is at least in part made from one or more materials selected from the group of TPE, PTFE, silicone and EPDM.

9. Medical device according to claim 1, wherein said medical device is a drug delivery system.

10. Medical device according to claim 1, further comprising a dispense interface comprising said first valve, said second valve, said first pre-valve ullage, said second pre-valve ullage and said post-valve ullage with said first proximal end and said second distal end.

* * * * *